(12) United States Patent
Clasen et al.

(10) Patent No.: US 10,786,139 B2
(45) Date of Patent: Sep. 29, 2020

(54) MIRROR SUCKER HAVING A SOLID MIRROR

(71) Applicant: Cleverdent Ltd., Münster (DE)

(72) Inventors: Stephan Clasen, Münster (DE); Martin Kayser, Cologne (DE)

(73) Assignee: Cleverdent Ltd., Münster (DE)

( * ) Notice: Subject to any disclaimer, the term of this patent is extended or adjusted under 35 U.S.C. 154(b) by 0 days.

(21) Appl. No.: 15/022,656

(22) PCT Filed: Sep. 18, 2014

(86) PCT No.: PCT/EP2014/002529
§ 371 (c)(1),
(2) Date: Mar. 17, 2016

(87) PCT Pub. No.: WO2015/039752
PCT Pub. Date: Mar. 26, 2015

(65) Prior Publication Data
US 2016/0227987 A1 Aug. 11, 2016

(30) Foreign Application Priority Data
Sep. 18, 2013 (DE) .................. 10 2013 110 302

(51) Int. Cl.
*A61B 1/247* (2006.01)
*A61B 1/00* (2006.01)
(Continued)

(52) U.S. Cl.
CPC ........ *A61B 1/00094* (2013.01); *A61B 1/0011* (2013.01); *A61B 1/247* (2013.01); *A61B 1/253* (2013.01); *A61C 17/08* (2019.05)

(58) Field of Classification Search
CPC ........... A61B 1/247; A61B 1/253; A61B 1/24; A61B 1/00094; A61B 1/0011; A61C 17/08
(Continued)

(56) References Cited

U.S. PATENT DOCUMENTS 236,040 A * 12/1880 Friedman ................ F28D 11/02
165/90
1,240,175 A * 9/1917 Burke ..................... B29C 70/78
156/242
(Continued)

FOREIGN PATENT DOCUMENTS

CN 2498989 7/2002
CN 102525389 7/2012
(Continued)

OTHER PUBLICATIONS

International Search Report and the Written Opinion dated Feb. 17, 2015 From the International Searching Authority Re. Application No. PCT/EP2014/002529 and Its Tranlsation of Search Report in English.
(Continued)

*Primary Examiner* — Heidi M Eide

(57) ABSTRACT

A dental mirror sucker (10) for extracting liquids and particles from an oral cavity of a patient, having a hollow base body (12), which has an outer surface (16), an inner surface (14), a longitudinal axis (X-X) and a suction opening (20), wherein the inner surface (14) has a mirror (22) which can be observed through the suction opening (20) and the base body (12) is formed from a first base body part (32) and a second base body part (34), which are connected to each other. The mirror sucker (10) is characterized in that the mirror (22) is held in a mirror receptacle (48) of the first base body part (32) having an opening (28), the inner wall (30) of which forms an upper support shoulder (40), which
(Continued)

contacts an outer wall (36) of the mirror (24), wherein the upper support shoulder (40) is formed by the first base body part (32) and encloses the entire outer circumference of the mirror (22); the opening (28) of the first base body part (34) tapers from a base body bottom side (42) in the direction of the suction opening (20) and has a diameter on the side thereof facing the base body bottom side (42) which is larger than the diameter of the mirror (22); and the two base body parts (32, 34) are connected to each other without a gap such that together they form the base body (12) in one piece.

21 Claims, 2 Drawing Sheets

(51) Int. Cl.
A61B 1/253 (2006.01)
A61C 17/08 (2006.01)

(58) Field of Classification Search
USPC .............. 433/30, 31, 91; 600/189, 246–248; 52/785.11
See application file for complete search history.

(56) References Cited

U.S. PATENT DOCUMENTS

| | | | | |
|---|---|---|---|---|
| 2,525,181 A * | 10/1950 | Ransdell | ................ | A61B 1/247 433/30 |
| 2,627,206 A * | 2/1953 | Clark | .................... | A61B 1/247 359/882 |
| 3,092,910 A * | 6/1963 | Warriner | ................ | A61B 1/253 433/31 |
| 3,102,338 A * | 9/1963 | Warriner | ................ | A61B 1/253 359/509 |
| 3,829,199 A | 8/1974 | Brown | | |
| 3,928,916 A * | 12/1975 | Hansson | .............. | A61C 17/043 433/31 |
| 4,713,002 A * | 12/1987 | Presser | ................. | A61B 1/247 433/30 |
| 4,900,253 A * | 2/1990 | Landis | ................... | A61B 1/247 250/504 H |
| 5,295,826 A * | 3/1994 | Yandell | ................ | A61C 17/043 433/30 |
| 5,428,484 A * | 6/1995 | Baker | .................... | A61B 1/247 359/872 |
| 5,490,780 A * | 2/1996 | Riewenherm | ........ | A61C 17/043 433/31 |
| 5,655,904 A * | 8/1997 | Usui | ...................... | A61B 1/253 433/30 |
| 5,722,830 A * | 3/1998 | Brandhorst | .......... | A61C 9/0026 433/89 |
| 5,951,284 A * | 9/1999 | Lake | ...................... | A61B 1/253 433/31 |
| 6,247,924 B1 * | 6/2001 | Gunnarsson | ........... | A61B 1/253 433/30 |
| 6,544,036 B1 * | 4/2003 | Brattesani | .............. | A61B 1/247 433/29 |
| 6,554,765 B1 * | 4/2003 | Yarush | ............... | A61B 1/00039 348/73 |
| 8,133,052 B1 * | 3/2012 | Emmons, III | ..... | A61B 1/00094 433/30 |
| 8,608,472 B2 * | 12/2013 | Clasen | ................. | A61C 17/043 433/29 |
| 2004/0115588 A1 * | 6/2004 | Sommers | ............... | A61B 1/247 433/31 |
| 2007/0148611 A1 * | 6/2007 | Frider | ................ | A61B 1/00094 433/31 |
| 2007/0287123 A1 * | 12/2007 | Swift | ................... | A61B 1/0011 433/30 |
| 2009/0061384 A1 * | 3/2009 | Thomssen | ................ | A61C 1/05 433/132 |
| 2009/0311648 A1 * | 12/2009 | Clasen | ................. | A61C 17/043 433/31 |
| 2010/0021860 A1 * | 1/2010 | Christman | ............. | A61B 1/247 433/96 |
| 2012/0021373 A1 * | 1/2012 | Moreno | ................. | A61B 1/015 433/31 |

FOREIGN PATENT DOCUMENTS

| | | | |
|---|---|---|---|
| CN | 202681906 | 1/2013 | |
| DE | 102012100119 | 12/2012 | |
| EP | 0314657 | 5/1989 | |
| FR | 2642298 A1 * | 8/1990 | ............. A61B 1/253 |
| GB | 1255719 A * | 12/1971 | ............. A61B 1/253 |
| WO | WO 2013104647 | 7/2013 | |
| WO | WO 2015/039752 | 3/2015 | |

OTHER PUBLICATIONS

Office Action dated Aug. 14, 2018 From the Israel Patent Office Re. Application No. 244650 and Its Translation Into English. (6 Pages).
Written Opinion dated Feb. 14, 2018 From the Intellectual Property Office of Singapore, IPOS Re. Application No. 11201602089R. (6 Pages).
Office Action dated Dec. 13, 2018 From the Israel Patent Office Re. Application No. 244650 and Its Translation Into English. (5 Pages).

* cited by examiner

MIRROR SUCKER HAVING A SOLID MIRROR

RELATED APPLICATIONS

This application is a National Phase of PCT Patent Application No. PCT/EP2014/002529 having International filing date of Sep. 18, 2014, which claims the benefit of priority of German Patent Application No. 10 2013 110 302.2 filed on Sep. 18, 2013. The contents of the above applications are all incorporated by reference as if fully set forth herein in their entirety.

FIELD AND BACKGROUND OF THE INVENTION

The invention relates to a dental mirror sucker for extracting liquids and particles from an oral cavity of a patient, with a hollow base body, which has an outer surface, an inner surface, a longitudinal axis and a suction opening, wherein the inner surface has a mirror that can be observed through the suction opening, and the base body is formed from a first base body part and a second base body part, which are securely connected to each other. The invention furthermore concerns a method for producing such a mirror sucker.

In the course of dental treatments it is often necessary to extract liquids or released particles, for example, saliva, spray water and blood, which have accrued during the treatment. Water, for example for cleaning purposes, or after use of a multifunction spray can also accumulate, and this must be extracted. For this purpose extractors are usually used, which as a rule are formed from a tubular body made of plastic, at the end of which is attached a hose, which in turn is connected with a pump. The bothersome liquids and solid bodies are led out through the hose.

Often an extractor is not used by the dentist or dental surgeon him/herself, but is guided and held by an assistant, because the dentist who is performing the treatment must hold a drill with the one hand, and a mirror with the other hand, with which he/she can view the region that is being treated. What is disadvantageous in the procedure as described is the fact that the two persons must stand or sit very close to one another around the region that has being treated. In particular, this can be perceived to be bothersome for the dentist performing the treatment, if the latter takes the form of relatively difficult or fine motorised demanding operations.

From DE 102006048463 A1 a medical mirror sucker is of known art, in which the inner surface has a mirrored surface that can be observed through the suction opening. The inventive reflective coating enables the user to use the medical mirror sucker both as a mirror sucker for the removal of liquids and particles, and at the same time also as a mirror. With the aid of such a mirror sucker he/she can now undertake the treatment without a person assisting. The mirror sucker is therefore used simultaneously as an extractor and as a mirror.

The basic idea of combining the two items of equipment is fundamentally very good, but the practical implementation of the idea and the production of such a mirror sucker has proved to be extremely difficult. The mirror must be securely framed; it may not be released, and should also not be allowed to move during the treatment, since the view is thereby impaired. Also, as far as possible, no unevennesses or gaps may be present, since the latter have a negative influence on the noise that is generated.

The base body of the mirror sucker can, for example, be formed from two welded longitudinal halves, which hold the mirror in a groove. However, welding of the longitudinal halves in a satisfactory manner is almost impossible; either a shadow gap is formed, or excess material is created during the welding process, which material must subsequently be removed. The shadow gap is unattractive, and liquids and bacteria can collect in it; the removal of the excess material is time-consuming and leads to visible alterations of the surface of the base body. The two longitudinal halves must moreover be produced with great precision, in order to ensure an attractive appearance after assembly and welding, in particular one that is free of gaps and/or excess material. These are particularly annoying, because the dentist performing the treatment detects with his/her fingers every unevenness, groove, or step in the longitudinal profile of the mirror sucker. In particular, even in the longitudinal direction only the smallest length tolerances of the two halves are acceptable; moreover the two halves may not be arranged, even to a minimal extent, such that they are displaced relative to one another in the longitudinal direction.

SUMMARY OF THE INVENTION

The task of the present invention consists in the provision of a mirror sucker, which has a sufficiently high-quality mirror surface in the region of the suction opening. At the same time the mirror sucker should be able to be produced cost effectively, and should have an attractive exterior. The disadvantages of the prior art should be avoided; in particular the mirror sucker should have no gaps, or only insignificant gaps, on its outer surface. Furthermore it is a task of the invention to recommend a method for producing a mirror sucker with the advantages cited.

In accordance with the invention the task is achieved by means of a mirror sucker with the features of patent claim 1. An inventive method of production is specified in patent claim 10.

Accordingly the mirror is formed from two base body parts, which are connected with each other, are preferably welded or bonded with adhesive, and thus form a one-piece mirror sucker. In the context of the invention "one-piece" means that after production the two base body parts can only be separated from one another once again by a destructive process.

The mirror is securely attached in the mirror sucker, which is advantageous in that in operational practice the base body and mirror can be dealt with as one unit. The mirror and mirror sucker can be sterilised together; any insertion and release of the mirror in operational practice is omitted.

In this context the term "secure" means that the mirror is held such that it cannot be lost; it cannot be released without destroying the mirror sucker or the mirror.

An important item of knowledge consists in the fact that an attractive exterior of the base body is achieved, if one of the two first base body parts is as large as possible, and the other base body part is as small as possible, and the smaller base body part only extends to a small extent in the longitudinal direction of the mirror sucker. By this means any bothersome groove or step occurring on the connecting surfaces between the base body parts is relatively short.

Furthermore, it is important that the smaller base body part, and the connection between the base body parts, is arranged in a region that the dentist performing the treatment does not touch at all, or only a little, during the treatment.

Even if the connecting surfaces have a negative effect on the surface of the mirror sucker, they do not lead to a haptic disturbance.

The arrangement in the region of the rear side of the mirror, that is to say, on the bottom side of the mirror sucker, is particularly advantageous because the said region as a rule cannot be observed when the mirror sucker is being used. Also, any alterations to the surface that are visible, but not tangible, attract hardly any attention.

The first base body part thus forms almost the whole of the base body of the mirror sucker, while the second base body part essentially just closes the opening that is necessary for purposes of inserting the mirror into the first base body part. With reference to the exterior surface the first base body part has a surface percentage of 80 to 95%, while the second base body part has a surface percentage of 5 to 20%.

The mirror is advantageously circular, but can also be oval, or other suitable shapes. In what follows the customary circular shape of the mirror will be assumed.

In order to maintain a reliable mirror in the long term, the first base body part has a mirror receptacle with an opening for purposes of inserting the mirror. The first base body part thus laterally surrounds the mirror inserted into the opening. In the complete mirror sucker the opening is closed on the rear side, that is to say, behind the inserted mirror, by the second base body part. The two base body parts are welded together, or bonded together with adhesive.

The material surrounding and holding the mirror is advantageously soft or elastic, such that it can compensate for any material expansions that occur, for example during sterilisation. Unwanted stresses in the region of the mirror, which can destroy the mirror and/or the base body, are by this means effectively avoided.

Alternatively or additionally, the mirror can be held in a groove, which is sufficiently deep in the lateral direction so as to compensate for any thermal expansion, i.e., any increase of the surface area and diameter of the mirror. The expanding mirror can expand into the sufficiently deep groove. Instead of the groove, the diameter of the opening in the first base body part, into which the mirror is inserted, can also have a somewhat larger diameter than the mirror.

The visible surface area of the mirror remains free, and can be observed from the front. In an advantageous variant of embodiment, the second base body part arranged on the rear side of the mirror has overall dimensions that only exceed the dimensions of the mirror by an insignificant extent. By this means it is possible, firstly to produce the first base body part, then to insert the mirror from behind into the free opening of the first base body part, and finally to close the opening from behind with the second base body part.

In accordance with the invention the opening in the first base body part tapers in the direction of a floor surface within the base body in the region of the suction opening; this is embodied and dimensioned such that the inserted mirror makes contact with an upper support shoulder in the mirror receptacle, which shoulder is formed in an inner wall of the opening.

It is important for the opening of the mirror receptacle of the first base body part to be dimensioned such that the mirror can be introduced into the mirror receptacle. For this reason the opening has, on its side facing the base body rear side, a diameter that exceeds the diameter of the mirror. Accordingly, the second base body part also has a diameter that exceeds the diameter of the mirror. Finally, in the direction of the vertical cross-section, the opening is a conically tapering passage into which the mirror is inserted from the wider side. These statements relate to a basic circular form of the mirror; if the latter has another form the mirror receptacle must be executed such that this other form can also be received.

In a particularly advantageous variant of embodiment the mirror, in its vertical cross-section, is executed in an essentially trapezoidal shape, wherein the diameter of the mirror, starting from the mirror surface, increases in the direction of the base body bottom side. As already explained, the inner wall of the opening of the first base body part, has a vertical cross-section corresponding to that of the mirror; its diameter increases starting from the base body bottom side.

The trapezoidal shape of the outer wall of the mirror and the inner wall of the opening, and the upper support shoulder, are advantageously selected such that, in the inserted state of the mirror, the visible mirror surface closes flush with the floor surface of the first base body part, which surrounds the mirror surface. As a result of contact with the outer side of the mirror, the upper support shoulder prevents the mirror from projecting upwards beyond the floor surface, or from being able to be released out of the base body in this direction.

Advantageously the mirror is held by a friction-fit or form-fit as it is inserted in the mirror receptacle. For example, the diameter of the opening can be executed so as to be minimally less than the diameter of the mirror. During insertion the mirror then deforms the surrounding material, pushing it back somewhat, such that the mirror is subsequently held by the elastic material. The second base body part is subsequently bonded with adhesive, or injection moulded, onto the first base body part with the mirror inserted and held.

Alternatively it is also conceivable that it is not the entire diameter of the opening that is less than the diameter of the mirror, rather than just a plurality, preferably three, projections are evenly distributed over the course of the inner wall or support shoulder; these hold the mirror in its position, before connection with the second base body part.

The mirror surface and the surrounding floor surface form an overall surface that is as flat as possible, over which the airflow, sucked-in liquid, and particles can be led away in an optimal manner. The overall flat surface also ensures that any noise generated by air turbulence in this region is at a low level. In the context of the invention a protrusion of the mirror, relative to the floor surface of the first base body part, of up to 0.3 mm is still regarded as flush.

As an alternative to the pure trapezoidal shape the mirror can, for example, have a maximum diameter in the central region of its vertical cross-section. Starting from the mirror surface, the diameter therefore firstly increases and then decreases once again in the direction of the rear side of the mirror. The inner wall of the opening is then designed correspondingly, so that the mirror can be clipped into the mirror-mounting groove formed. The inner wall of the opening then forms not only an upper support shoulder, but also a lower support shoulder. It is also conceivable for the lower support shoulder, which makes contact with the mirror starting from its rear side up to its maximum diameter, to be formed by the second base body part.

The second base body part can be connected with the first base body part and can have an appropriate shape, such that it presses the mirror within the opening against the upper support shoulder with a preload. This ensures that the mirror is securely held, and also cannot move during the treatment. The inner wall of the opening acts as a sealing lip, and makes contact with the circumference of the mirror side face in a manner similar to that of an oil seal.

A thermoplastic plastic is particularly suitable for production, for example, polypropylene, or also polyethylene. The external appearance of the mirror sucker can be influenced by the introduction of additives. In accordance with the invention production in polyester has also proved to be advantageous. With regard to the surface finish of the finished product, polyester has significant advantages compared with other plastics, for example, with regard to an adjustable gloss level, scratch resistance, together with surface smoothness. Glass beads, for example, come into consideration as a suitable additive for purposes of influencing the material properties; amongst other properties, these influence the gloss level of the surface.

The suction opening of the tubular base body does not run at right angles to the longitudinal axis, but rather is executed at an angle to the latter. By this means an angled form of the mirror sucker ensues, as a result of which the latter can be introduced more easily, for example, between cheek and teeth. The mirror is not located in front of the suction opening, but rather essentially behind the suction opening, in the flow direction of the sucked-in air, that is to say, within the base body. This ensures that the mirror sucker is not extended in terms of a front-mounted mirror, which would reduce the suction power.

Although adhesive bonding of the base body parts with one another is possible in principle, it has proved to be particularly advantageous to weld the two base body parts together, and not to use any adhesive. The disadvantages inherently connected with adhesive can thereby be avoided.

The inventive method for producing the mirror sucker has the following steps:

production of the first base body part with a mirror receptacle for the mirror, which has the opening with an essentially circumferential upper support shoulder, insertion of the mirror into the mirror receptacle, such that the upper support shoulder makes contact with a face of the mirror, production of a second base body part and connection of the second base body part with the first base body part in the region of the mirror rear side, such that the two base body parts form a one-piece base body.

The first base body part can advantageously be produced and embodied such that the mirror, even before the connection of the two base body parts, with each other, is held in the first base body part by a friction-fit or form-fit. This simplifies the following steps in production.

The method is thus quick and simple to execute. By virtue of the relatively simple basic shape of the second base body part the design of the tool for production is also rather simple, and the reliability of the tool in production is high.

BRIEF DESCRIPTION OF THE SEVERAL VIEWS OF THE DRAWINGS

The invention is described in more detail on the basis of the following figures. These simply show examples of embodiment; the invention is not to be limited to these.

Here.

DESCRIPTION OF SPECIFIC EMBODIMENTS OF THE INVENTION

Figure 1:
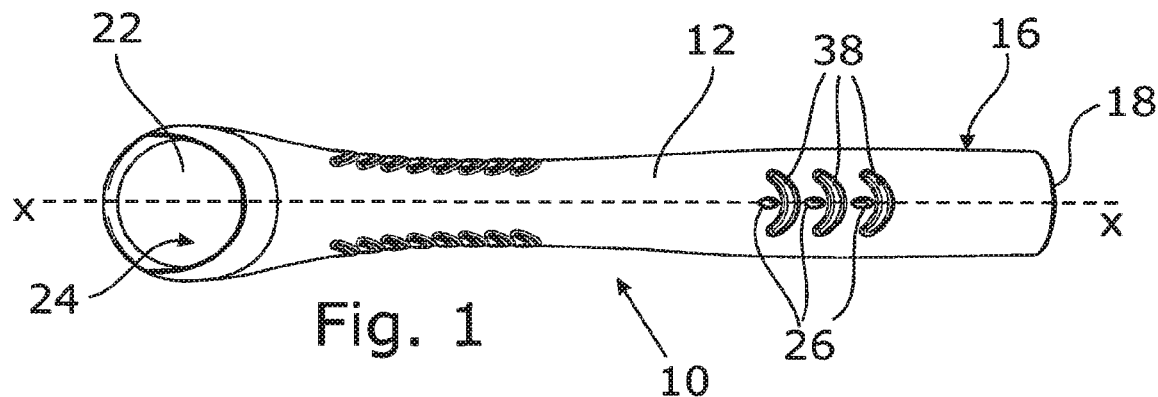
FIG. 1: shows an inventive mirror sucker from above.
Figure 2:
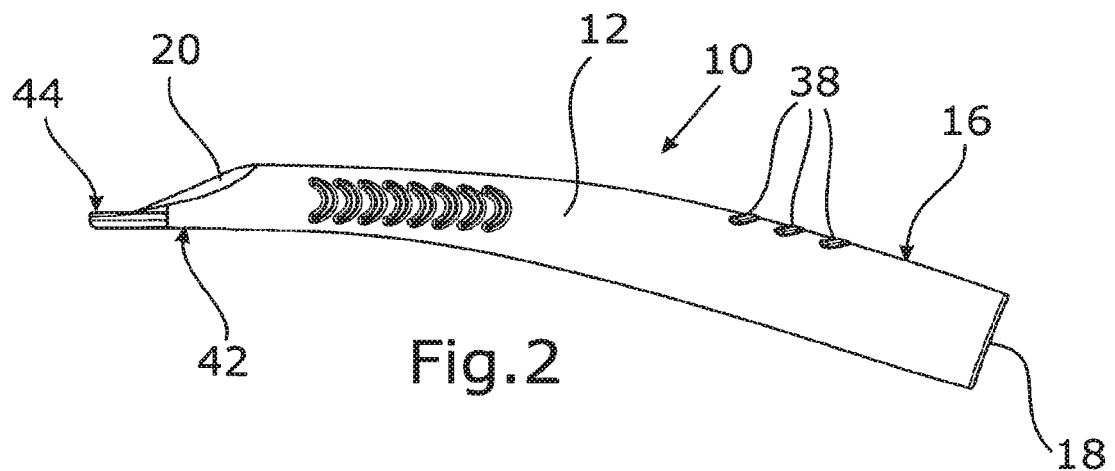
FIG. 2: shows the inventive mirror sucker in FIG. 1 from the side.
Figure 3:
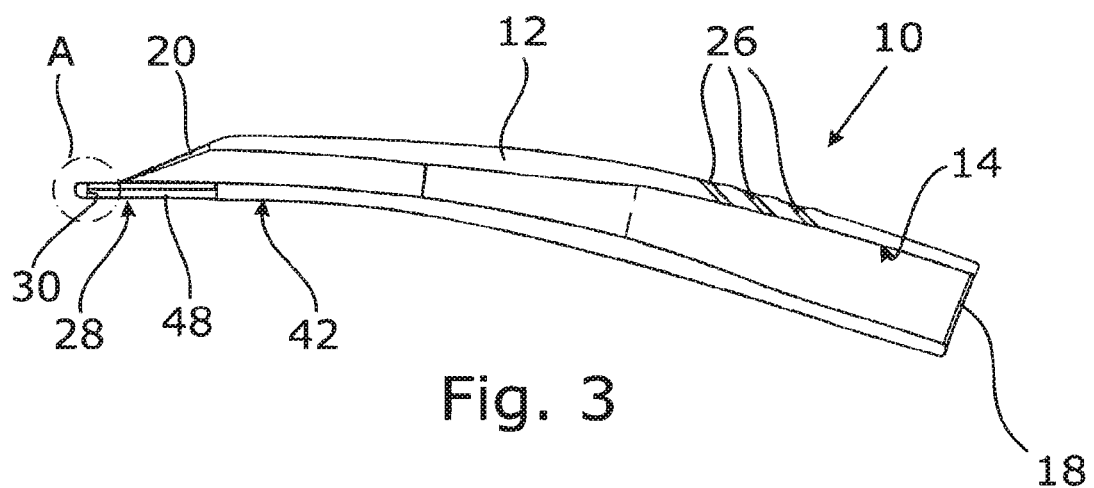
FIG. 3: shows the inventive mirror sucker in FIG. 1 in a longitudinal section.

As can be seen in particular from FIGS. 1, 2 and 3 an inventive mirror sucker 10 has a hollow tubular base body 12 with an inner surface 14 and an outer surface 16. Furthermore, the base body 12 has a longitudinal axis X-X (cf. FIG. 1). The curved shape of the mirror sucker 10, which can be discerned in particular in FIGS. 2 and 3, has the advantage that this can be guided more easily to the location that is being treated.

The base body 12 has a connection port 18 for a hose, not shown, and a suction opening 20 for purposes of extracting particles and liquids. The liquids or particles to be extracted are sucked in through the suction opening 20 and are led away through the connection port 18 via the hose.

In accordance with the invention a mirror 22 is arranged within the base body 12 in the region of the suction opening 20, which mirror can be observed through the suction opening 20. Accordingly, a visible mirror surface 24 faces the suction opening 20. The mirror 22 is completely within the base body 12, that is to say, in the flow direction of the air that is being extracted, it is arranged behind the suction opening 20. The air that is being sucked in is led over the mirror surface 24, as a result of which any fogging of the mirror surface 24 is effectively prevented.

The mirror sucker 10 has additional openings 26, through which air is similarly sucked in. The additional openings 26 prevent any under-pressure within the base body 12 if, for example, the suction opening 20 is closed by the tongue or cheek of the patient. In the example of embodiment shown three additional openings 26 are provided, however, it is also conceivable to have only one additional opening 26, or also more than three additional openings 26.

Profile elements 38 can be discerned on the outer surface 16 of the base body 12; these provide a secure grip on the mirror sucker 10, and prevent the fingers of the dentist performing treatment from slipping.

Figure 6:
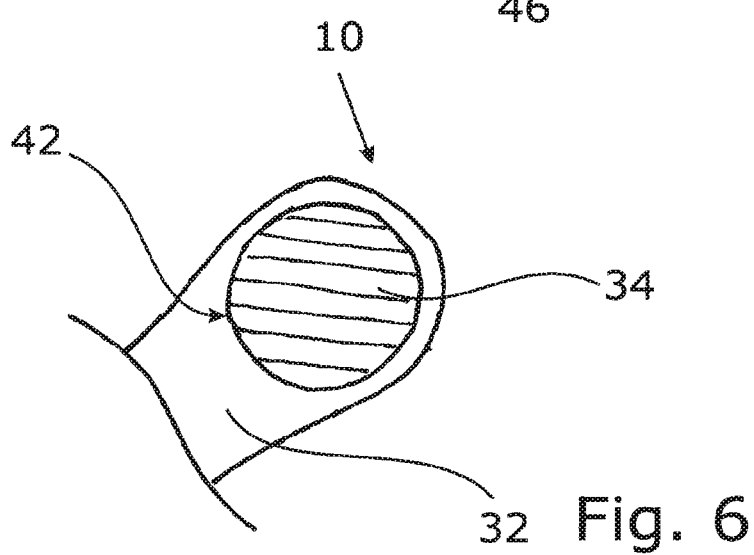
FIG. 6: shows a simplified representation of the front region of the mirror sucker from below.

FIGS. 3 and 6 show that the base body 12 is formed from a first base body part 32 and a second base body part 34. The first base body part 32 has a mirror receptacle 48 with an opening 28, into which the mirror 22 is inserted in the assembled state. An inner wall 30 of the opening 28 surrounds the mirror 22 and makes contact with an outer wall 36 of the mirror 22 in at least some regions. The opening 28 tapers from a base body bottom side 42 in the direction of the suction opening 20. On its side facing the base body bottom side 42 the opening 28 has a diameter that is larger than the diameter of the mirror 22. This is a prerequisite such that the mirror 22 can be introduced into the mirror receptacle 48.

Figure 5:
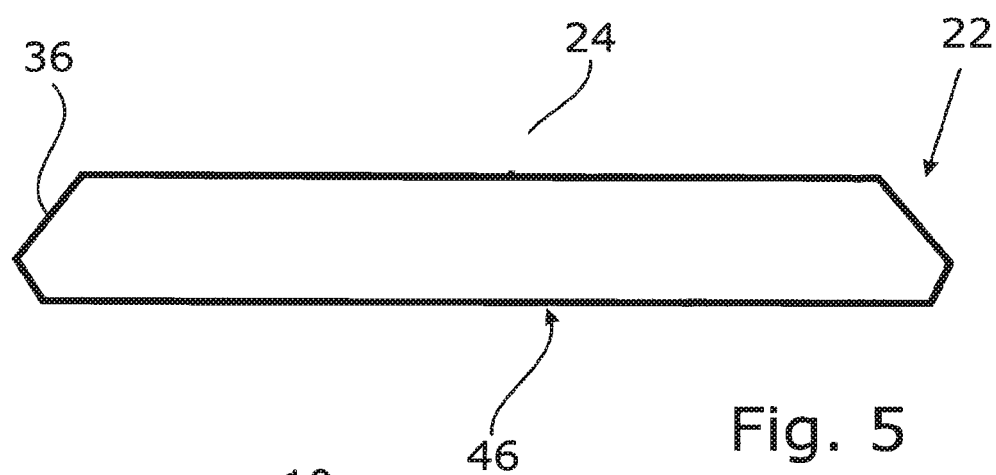
FIG. 5: shows a mirror in side view.

In cross-section the mirror 22 is executed so as to be approximately trapezoidal in shape, at least in some sections (cf. FIG. 5), so that its diameter increases, at least in some sections, starting from the mirror surface 24 in the direction of a base body bottom side 42. The mirror 22 has a mirror rear side 46, facing away from the visible mirror surface 24. FIG. 5 shows a form of embodiment in which the mirror 22 has a machined diameter in the vertical direction, approximately in the lower third. This shape simplifies the insertion or clipping into the mirror receptacle 48. A lower support shoulder makes contact with the lower region of the outer wall 36.

Figure 4:
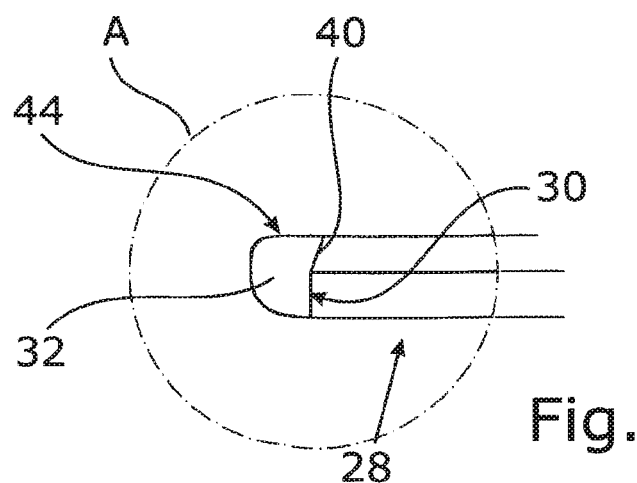
FIG. 4: shows an enlargement of the region A in FIG. 3.

FIG. 4 illustrates in an enlarged representation the region A in FIG. 4, in which an upper support shoulder 40 surrounds the entire outer wall 36 of the mirror 22, and seals a space alongside and below the mirror 22. The sealing is improved by preloading the upper support shoulder 40. This means that the mirror 22, when inserted into the first base body part 32, is pressed against the upper support shoulder 40, and the latter is minimally compressed or elastically deformed.

Furthermore, this variant of embodiment has the advantage that the mirror 22 is let almost flush into a floor surface 44.

FIG. 6 shows the front region of the mirror sucker 10 with a view onto the base body bottom side 42. The second base body part 34 can be discerned (cross-hatched); this closes the opening 28.

The invention is not limited to the examples of embodiment described, but rather comprises all forms of embodiment that operate in the same manner. The variant of embodiment described is only an example, and is not to be understood as restrictive. It is also possible to combine the technical features shown with one another in any technically feasible manner.

What is claimed is:

1. A dental mirror sucker (10) for extracting liquids and particles from an oral cavity of a patient, comprising:
   a hollow tubular base body (12), which has an inner surface (14), an outer surface (16), a longitudinal axis (X-X), a connection port (18) for a hose, and a suction opening (20),
   wherein the inner surface (14) has a mirror (22) with a mirror surface (24) and a mirror rear side (46), whereas the mirror surface (24) can be observed through the suction opening (20),
   wherein the base body (12) is formed from a first base body part (32) and a second base body part (34),
   wherein the mirror (22) is held in a mirror receptacle (48) of the first base body part (32) in an opening (28), an inner wall (30) of which forms an upper support shoulder (40), which makes contact with an outer wall (36) of the mirror (24), wherein the upper support shoulder (40) is formed by the first base body part (32) and surrounds an entire outer circumference of the mirror (22),
   wherein the opening (28) of the first base body part (34) tapers from a base body bottom side (42) in a direction of the suction opening (20), whereas the opening (28) on a side facing the base body bottom side (42) has a diameter that is larger than a diameter of the mirror (22), wherein the two base body parts (32, 34) are joined together without any gaps such that they together form a one-piece base body (12);
   wherein the first base body part and the second base body part are produced independently from each other and connected to each other in a region of the mirror rear side;
   wherein the mirror is secured unreleasably in the mirror receptacle, such that the mirror cannot be removed from the mirror receptacle without destroying at least one of the base body and the mirror;
   wherein the mirror surface (24) and the surrounding floor of the inner surface (14) of the tubular base body (12) form a flat surface to minimize noise generated by air turbulence in this region,
   wherein the second base body part (34) is arranged on the rear side of the mirror (22) within the opening (28) of the mirror receptacle (48) and just closes the opening (28) that is necessary for purpose of inserting the mirror (22) into the first base body part (32);
   wherein the first base body part (34) is made of an elastic material and the mirror having a larger diameter than the opening (28) such that the mirror (28) is frictionally held in the first base body part (34).

2. The dental mirror sucker (10) in accordance with claim 1, wherein the second base body part (34) makes contact with a mirror rear side (46).

3. The dental mirror sucker (10) in accordance with claim 2, wherein the inner wall (30) of the opening (28) forms a lower support shoulder, which makes contact with the outer wall (36) of the mirror (22).

4. The dental mirror sucker (10) in accordance with claim 2, wherein the mirror (22) is held without adhesive bonding in the first base body part (32).

5. The dental mirror sucker (10) in accordance with claim 1, wherein the inner wall (30) of the opening (28) forms a lower support shoulder, which makes contact with the outer wall (36) of the mirror (22).

6. The dental mirror sucker (10) in accordance with claim 5, wherein the mirror (22) is held without adhesive bonding in the first base body part (32).

7. The dental mirror sucker (10) in accordance with claim 1, wherein the second base body part (32) forms a lower support shoulder.

8. The dental mirror sucker (10) in accordance with claim 1, wherein the mirror (22) is held without adhesive bonding in the first base body part (32).

9. The dental mirror sucker (10) in accordance with claim 8, wherein the base body parts (32, 34) are produced from plastic.

10. The dental mirror sucker (10) in accordance with claim 1, wherein the base body parts (32, 34) are produced from plastic.

11. The dental mirror sucker (10) in accordance with claim 10, wherein the two base body parts (32, 34) are welded together.

12. The dental mirror sucker (10) in accordance with claim 11, wherein the second base body part (34) is injection moulded onto the first base body part (32).

13. The dental mirror sucker (10) in accordance with claim 10, wherein the second base body part (34) is injection moulded onto the first base body part (32).

14. The dental mirror sucker (10) in accordance with claim 1, wherein said mirror surface (24) and said mirror rear side (46) are opposite to one another.

15. The dental mirror sucker (10) in accordance with claim 1, wherein lateral walls of the second base body part (34) are surrounded by the inner wall (30) of the opening and 80% to 95% of an exterior surface of the base body (12) is an exterior surface of the first base body part and 5% to 20% of the exterior surface of the base body (12) is the exterior surface of the second base body part.

16. The dental mirror sucker (10) in accordance with claim 1, wherein the first base body part has a surface percentage of 80 to 95% of the exterior surface and the second base body part has a surface percentage of 5% to 20% of the exterior surface.

17. The dental mirror sucker (10) in accordance with claim 1, wherein an orientation of at the suction opening (20) along the longitudinal axis (X-X) is angled relative to the orientation of the longitudinal axis (X-X) at the connection port (18), and the mirror surface (24) is oriented substantially perpendicular to the orientation of the longitudinal axis (X-X) at the suction opening (20).

18. The method in accordance with claim 1, wherein the upper support shoulder (40) prevents the mirror from projecting upwards beyond a floor surface within the base body in the suction opening and from being released out of the base body.

19. A method for producing a dental mirror sucker (10) for extracting liquids and particles from an oral cavity of a patient, wherein the dental sucker comprises a hollow base body (12), which has an outer surface (16), an inner surface (14), a longitudinal axis (X-X), and a suction opening (20), wherein the inner surface (14) has a mirror (22) with a mirror surface (24) and mirror rear side (46), whereas the mirror surface (24) can be observed through the suction opening (20), the method comprising:

production of a first base body part (32) with a mirror receptacle for the mirror (22), which has an opening (28) with a circumferential upper support shoulder (40);

insertion of the mirror (22) into the mirror receptacle, such that the upper support shoulder (40) makes contact with an outer wall (36) of the mirror (22), production of a second base body part (34), and connection of the second base body part (34) with the first base body part (32) in a region of a mirror rear side (46), such that the two base body parts (32, 34) form a one-piece base body (12), wherein the first base body part and the second base body part are produced independently from each other and connected to each other;

wherein the mirror is secured unreleasably in the mirror receptacle, such that the mirror cannot be removed from the mirror receptacle without destroying at least one of the base body and the mirror;

wherein the mirror surface (24) and the surrounding floor of the inner surface (14) of the tubular base body (12) form a flat surface to minimize noise generated by air turbulence in this region, wherein the second base body part (34) is arranged on the rear side of the mirror (22) within the opening (28) of the mirror receptacle (48) and just closes the opening (28) that is necessary for purpose of inserting the mirror (22) into the first base body part (32);

wherein the first base body part (34) is made of an elastic material and the mirror having a larger diameter than the opening (28) such that the mirror (28) is frictionally held in the first base body part (34).

20. The method in accordance with claim 19, wherein both base body parts (32, 34) are produced from plastic, and the second base body part (34) is injection moulded onto the first base body part (32).

21. The method in accordance with claim 19, wherein the dental sucker (10) further comprises a connection port (18), and an orientation of the suction opening (20) along the longitudinal axis (X-X) is angled relative to the orientation of the longitudinal axis (X-X) at the connection port (18), and the mirror surface (24) is oriented substantially perpendicular to the orientation of the longitudinal axis (X-X) at the suction opening (20).

* * * * *